(12) United States Patent
Yamamoto et al.

(10) Patent No.: US 8,987,005 B2
(45) Date of Patent: Mar. 24, 2015

(54) REAGENT FOR MEASURING AGGLUTINATION AND METHOD OF MEASURING AGGLUTINATION

(75) Inventors: Mitsuaki Yamamoto, Ryugasaki (JP); Tadaaki Yoshida, Ryugasaki (JP)

(73) Assignee: Sekisui Medical Co., Ltd., Tokyo (JP)

( * ) Notice: Subject to any disclaimer, the term of this patent is extended or adjusted under 35 U.S.C. 154(b) by 579 days.

(21) Appl. No.: 12/086,600

(22) PCT Filed: Dec. 27, 2006

(86) PCT No.: PCT/JP2006/326030
§ 371 (c)(1),
(2), (4) Date: Jun. 16, 2008

(87) PCT Pub. No.: WO2007/074860
PCT Pub. Date: Jul. 5, 2007

(65) Prior Publication Data
US 2010/0167310 A1     Jul. 1, 2010

(30) Foreign Application Priority Data

Dec. 28, 2005  (JP) ................................ 2005-379307

(51) Int. Cl.
G01N 33/546   (2006.01)
G01N 33/542   (2006.01)
G01N 33/545   (2006.01)
G01N 33/543   (2006.01)

(52) U.S. Cl.
CPC ................................ *G01N 33/54313* (2013.01)
USPC ........... 436/533; 436/501; 436/531; 436/532; 436/534

(58) Field of Classification Search
None
See application file for complete search history.

(56) References Cited

U.S. PATENT DOCUMENTS

| | | | |
|---|---|---|---|
| 4,362,531 A * | 12/1982 | de Steenwinkel et al. | 436/512 |
| 5,506,151 A * | 4/1996 | Ito et al. | 436/533 |
| 6,777,246 B2 * | 8/2004 | Lawrence et al. | 436/533 |
| 6,825,000 B1 * | 11/2004 | Yokoi et al. | 435/7.92 |
| 2005/0069967 A1 | 3/2005 | Sumida et al. | |

FOREIGN PATENT DOCUMENTS

| | | |
|---|---|---|
| CN | 1533275 A | 9/2004 |
| CN | 1610547 A | 4/2005 |
| EP | 1 079 231 A1 | 2/2001 |
| EP | 1 321 770 A2 | 6/2003 |
| JP | 04-048265 A | 2/1992 |
| JP | 7-229900 A | 8/1995 |
| JP | 11-344493 A | 12/1999 |
| JP | 2000-258419 A | 9/2000 |
| JP | 2004-108850 A | 4/2004 |
| JP | 2005-106609 A | 4/2005 |
| WO | WO 02/078693 A2 | 10/2002 |
| WO | WO 03/007947 A1 | 1/2003 |

OTHER PUBLICATIONS

Bernard et al., "Latex immunoassay of urinary albumin," J. Clin. Chem. Clin. Biochem., 1983, vol. 21, No. 1, pp. 25-30.*
Bovaird et al., "Optimizing the o-phenylenediamine assay for horseradish peroxidase: effects of phosphate and pH, substrate and enzyme concentrations, and stopping reagents," Clin. Chem., 1982, vol. 28, No. 12, pp. 2423-2426.*
Chinese Office Action issued in Chinese Application No. 200680049621.1 on Mar. 20, 2013.
European Office Action issued in European Patent Application No. 06 843 412.5 on Oct. 6, 2014.

* cited by examiner

*Primary Examiner* — Galina Yakovleva
(74) *Attorney, Agent, or Firm* — Birch, Stewart, Kolasch & Birch, LLP (57) ABSTRACT

[PROBLEMS] To provide a reagent for measuring agglutination by using a reaction accelerator, which causes no spontaneous agglutination of receptor-sensitized carrier particles in the coexistence of these carrier particles, and a measurement method.

[MEANS FOR SOLVING PROBLEMS] A reagent for measuring agglutination by using a specific amine compound, whereby aggregation based on a specific reaction can be accelerated without causing spontaneous agglutination of carrier particles, and measurement method.

23 Claims, 2 Drawing Sheets

REAGENT FOR MEASURING AGGLUTINATION AND METHOD OF MEASURING AGGLUTINATION

TECHNICAL FIELD

The present invention relates to a reagent for measuring agglutination which is used in measuring a ligand through an agglutination reaction of an insoluble carrier particle sensitized with a specific receptor, and a measurement method for agglutination.

BACKGROUND ART

A measurement method of detecting an agglutination reaction has been conventionally and widely-used (applied) in a method such as a plate agglutination test. In particular, an immune agglutination method utilizing an antigen-antibody reaction has been mainly used because of the excellence in sensitivity, specificity, and reproducibility thereof.

Recently, the use of an insoluble carrier particle sensitized with an antibody which specifically recognizes a target ligand as an antigen and a widely-used automatic analyzer has enabled simple measurement of the ligand with higher sensitivity. Therefore, the immune agglutination method is widely-used in a clinical test and the like. The immune agglutination method is a method of measuring a concentration of a target ligand performed by allowing an insoluble carrier particle to agglutinate on the basis of the antigen-antibody reaction and optically measuring a degree of the obtained agglutination. As the insoluble carrier particle, a latex is commonly used. In this case, the method is particularly called a latex turbidimetric immunoassay (hereinafter abbreviated as an LTIA method).

It has been known, in the LTIA method, addition of an agglutination accelerator such as sodium chloride or guanidines accelerates formation of immune agglutination and improves measurement sensitivity (Patent Document 1).

However, coexistence of those agglutination accelerators with antibody-sensitized latexes resulted in nonspecific aggregation of the antibody-sensitized latexes (also called spontaneous aggregation) irrelevant to an immune reaction. There was a problem that after a long-term storage in the coexistence state, the particles were finally precipitated. Therefore, as a measurement reagent for the LTIA method, a two-shot reagent format is commonly used. The antibody-sensitized latex and the agglutination accelerator are separately prepared as constituent reagents and mixed together when measurement is performed.

In Patent Document 2, a method of dissolving aminosulfonate into a reagent to disperse a latex reagent is disclosed, because aminosulfonate suppresses nonspecific aggregation derived from a component of a measurement sample in a latex agglutination reaction, and is excellent in storage stability.

In addition, Patent Document 3 discloses a stabilization method, in which amino acid ester or polyamine is allowed to coexist in a latex reagent to enable stabilization of proteins, whereby nonspecific aggregation of proteins each bonded to a latex with one another is suppressed.

However, those documents only describe stabilization of the reagent that the nonspecific aggregation of latexes is suppressed, and do not describe an effect of accelerating an agglutination reaction.

Besides, even in the case where sodium chloride or guanidines was used as a reaction accelerator, satisfactory measurement sensitivity was not necessarily obtained when measurement time was limited as in the case of measurement using an automatic analyzer. Therefore, provision of a reaction accelerator having a higher effect has been expected.

Patent Document 1: JP 11-344493 A
Patent Document 2: JP 07-229900 A
Patent Document 3: JP 2004-108850 A

DISCLOSURE OF THE INVENTION

Problem to be solved by the Invention

The present invention is provided to solve the above-mentioned conventional technical problems. An object of the present invention is to provide a reagent for measuring agglutination using an organic amine compound which does not cause spontaneous agglutination of a receptor-sensitized latex even the receptor-sensitized latex coexists with the organic amine compound, and a measurement method therefor.

Moreover, another object of the present invention is to provide a reagent for measuring agglutination using an organic amine compound that is superior in a reaction accelerating effect to a conventional reaction accelerator such as sodium chloride or guanidines, and a measurement method therefor.

Means for solving the Problems

The inventors of the present invention intensively studied a compound that did not cause spontaneous agglutination of a receptor-sensitized latex in a measurement method for latex agglutination. As a result, the inventors found that certain kinds of organic amine compounds had an effect of accelerating an agglutination reaction without causing spontaneous agglutination of the receptor-sensitized latex, whereby the present invention was completed.

In addition, the inventors found that some of those organic amine compounds had a reaction accelerating effect superior to that of conventional reaction accelerators to thereby complete the present invention.

That is, the present invention has the following constitutions.

(1) A reagent for measuring agglutination including an insoluble carrier particle sensitized with a receptor specifically reacting with a target ligand and an organic amine compound.

(2) A reagent for measuring agglutination according to the item (1), in which the organic amine compound is one or more of the compounds selected from 2-amino-2-thiazoline hydrochloride, benzamidine hydrochloride, benzylamine hydrochloride, guanidine hydrochloride, aminopyrine, antipyrine, 4-aminoantipyrine, o-phenylenediamine dihydrochloride, p-anisidine hydrochloride, diphenhydramine hydrochloride, 2,4-diaminoanisole dihydrochloride, pyridine hydrochloride, 1,4-phenylenediamine hydrochloride, aminoguanidine hydrochloride, and betaine hydrochloride.

(3) A reagent for measuring agglutination according to the item (1) or (2), in which the insoluble carrier particle includes a latex.

(4) A reagent for measuring agglutination according to any one of the items (1) to (3), in which the receptor includes an antibody such as a polyclonal antibody, a monoclonal antibody, or a fragment including a reactive site thereof, and agglutination derived from immunoreaction is measured.

(5) A reagent for measuring agglutination according to any one of the items (1) to (4), in which the target ligand is any one or more of the selected ligands from C-reactive protein (CRP), FDP, D-dimer, prostate-specific antigen (PSA), hemoglobin A1c, albumin, pepsinogen I (PGI), pepsinogen II (PGII), matrix metalloproteinase (MMP), trypsin, chymotrypsin, elastase, and cathepsin.

(6) A reagent for measuring agglutination according to any one of the items (1) to (5) including 50 to 1,000 mM of the organic amine compound.

(7) A reagent for measuring agglutination according to any one of the items (1) to (6), in which the organic amine compound has a accelerating action of an agglutination reaction and a stabilizing action of particle dispersibility.

(8) A reagent for measuring agglutination according to the item (1) including the insoluble carrier particle sensitized with a receptor specifically reacting with the target ligand, and the organic amine compound in a state of coexistence.

(9) A reagent for measuring agglutination according to the item (1), in which the target ligand includes two or more kinds of ligands, and each of the insoluble carrier particles is sensitized with a receptor that specifically react with the target ligands.

(10) A method of measuring a time-dependent change of an agglutination reaction caused by adding to a target ligand an insoluble carrier particle sensitized with a receptor that specifically reacts with the ligand, including allowing an organic amine compound to coexist at least when the reaction is performed.

(11) A measurement method according to the item (10) including using the insoluble carrier particle with which the organic amine compound is preliminarily allowed to coexist.

(12) A measurement method according to the item (11), in which the target ligand includes two or more kinds, a time-dependent change of an agglutination reaction is measured, the reaction being caused by adding an insoluble carrier particle sensitized with a receptor R1 that specifically reacts with a ligand L1, and a time-dependent change of an agglutination reaction is measured, the reaction being caused by further adding an insoluble carrier particle sensitized with a receptor R2 that specifically reacts with a different ligand L2 after the reaction becomes substantially steady, or after the reaction is allowed to be substantially steady or simultaneously when the reaction is allowed to be substantially steady.

(13) A measurement method according to the item (12), in which a method of allowing the reaction to be substantially steady is performed by adding the R1 specifically reacting with the L1 in a free state.

(14) A measurement method according to any one of the items (10) to (13), in which the receptor includes an antibody such as a polyclonal antibody, a monoclonal antibody, or a fragment including a reactive site thereof.

(15) A stabilizer for particle dispersibility, which is used for a reagent for measuring agglutination, containing an organic amine compound.

(16) A method of stabilizing particle dispersibility of a reagent for measuring agglutination, including adding an organic amine compound to the reagent for measuring agglutination.

Effects of the Invention

A reagent for measuring agglutination using the organic amine compound of the present invention has the following effects.

(1) The reagent for measuring agglutination can be prepared as a one-shot reagent obtained by allowing a reaction accelerator to preliminarily coexist with a receptor-sensitized latex, because the reagent is unlikely to cause spontaneous agglutination of the receptor-sensitized latex even in the coexistence of the both substances.

(2) When the reagent for measuring agglutination is prepared as a one-shot reagent, measurement is possible by a one-step reaction, so the measurement time can be shortened to half or less of the time required for a case using a conventional two-shot reagent. In addition, when a reaction is performed using the one-shot reagent for the same amount of time as that required for measurement of the case using the conventional two-shot reagent, higher measurement sensitivity can be obtained.

(3) Besides, use of two kinds of the above-mentioned one-shot reagents in combination in a measurement system for a two-shot reagent enables consecutive measurement of two kinds of ligands in the same reaction vessel. The effect is particularly effective for calculation of a PGI/PGII ratio required for determination of a content ratio of two kinds of ligands in the same sample and an examination of HbA1c (%).

(4) Excellence of the organic amine compound in a reaction accelerating effect of the agglutination reaction can contribute to reduction of a reaction time, eventually reduction of a measurement time, and/or improvement of measurement sensitivity.

BEST MODE FOR CARRYING OUT THE INVENTION (Sample to be Measured)

Samples to be measured for a measurement reagent of the present invention, for example, include blood, serum, plasma, a supernatant of cultured lymphocytes, urine, spinal fluid, saliva, sweat, ascites, and an extract of cells or organs.

(Ligand)

As a target ligand in the present invention, any ligand can be a subject to be measured as long as the ligand can be measured by an agglutination method. Specific examples of the ligand include proteins such as C-reactive protein (CRP), FDP, D-dimer, prostate-specific antigen (PSA), hemoglobin A1c, albumin, pepsinogen I (PGI), pepsinogen II (PGII), matrix metalloproteinase (MMP), trypsin, chymotrypsin, elastase, and cathepsin; peptides; saccharides; nucleic acids; and lipids; and the like.

(Receptor)

As a receptor used in the present invention, a substance to which the target ligand specifically binds is used. In general, an anti-ligand polyclonal antibody and an anti-ligand monoclonal antibody can be used, which are obtained by immunizing rabbits, sheep, goats, and the like with the target ligand. Of those, use of the monoclonal antibody is particularly desirable from the viewpoint of specificity. The intact antibody may be used, or a fragment of the antibody obtained by cutting the antibody with an enzyme according to a conventional method may also be used.

In addition, when the subject to be measured is an antibody, an antigen can be used as a receptor. Moreover, a lectin, a nucleic acid, or the like can be used as a receptor depending on the kind of ligand.

(Carrier Particle)

An insoluble carrier particle sensitized with a receptor used in the present invention is not particularly limited, and a latex is preferable. As a material for the latex, any material can be used as long as the material is suitable for a method of sensitizing a receptor. In addition to a latex mainly composed of polystyrene, which is commonly used in an agglutination method, a styrene-butadiene copolymer, a (meth)acrylic acid ester polymer, and the like can be exemplified. In addition, a particle formed of a material such as metal colloid, gelatin, liposome, a microcapsule, silica, alumina, carbon black, a metal compound, a metal, a ceramic, a magnetic substance, or the like can also be used. As a method of sensitizing a receptor on a carrier particle, a chemical bonding method can also be used other than a commonly-used physical adsorption method.

The carrier particles of the same kind, or two or more kinds of materials or diameters can be used in the present invention.

(Organic Amine Compound)

Any organic amine compound may be used as long as the organic amine compound accelerates an agglutination reaction, and/or is unlikely to cause spontaneous aggregation of the carrier particles when the organic amine compound is allowed to coexist with the carrier particles sensitized with a receptor.

Whether a certain organic amine compound is unlikely to cause spontaneous aggregation of the carrier particles or not can be confirmed by a screening method described below. Moreover, whether the organic amine compound accelerates an agglutination reaction or not can be confirmed by comparing the degree of agglutination when the organic amine compound is used with the degree of agglutination when the organic amine compound is not used. After the results are confirmed, the organic amine compound can be readily evaluated to make a selection decision.

To be specific, one or more of compounds selected from 2-amino-2-thiazoline hydrochloride, benzamidine hydrochloride, benzylamine hydrochloride, guanidine hydrochloride, aminopyrine, antipyrine, 4-aminoantipyrine, o-phenylenediamine dihydrochloride, p-anisidine hydrochloride, diphenhydramine hydrochloride, 2,4-diaminoanisole dihydrochloride, pyridine hydrochloride, 1,4-phenylenediamine hydrochloride, aminoguanidine hydrochloride, and betaine hydrochloride are preferably used. Of those, benzamidine hydrochloride, benzylamine hydrochloride, and 2-amino-2-thiazoline hydrochloride are more preferably used.

Note that salts of each of the organic amine compounds are not particularly limited. Examples of those salts include sulfates, nitrates, hydrobromides, hydrofluorides, hydrofluoroborates, oxalates, lactates, adipates, tartrates, hydroiodides, toluenesulfonates, malonates, and bicarbonates. Suitable salts can be selected in consideration of handling easiness or easy availability as a reagent or the like in addition to the effects of the present invention.

The organic amine compound may have any concentration as long as the organic amine compound accelerates an agglutination reaction compared with the case where the organic amine compound is not added, and/or the organic amine compound has a concentration at which spontaneous aggregation is not likely to occur when carrier particles are allowed to coexist. A preferable concentration of the organic amine compound is 50 to 1,000 mM. Each of the optimal concentrations of the organic amine compounds used can be experimentally investigated according to the description of the present specification.

The term spontaneous aggregation in the present invention signifies aggregation of carrier particles not derived from a specific binding between a ligand and a receptor. The term stabilizing action of particle dispersibility in the present invention signifies an action that coexistence of an organic amine compound in a reagent containing receptor-sensitized insoluble carrier particles is unlikely to cause a spontaneous aggregation of the receptor-sensitized insoluble carrier particles. The latter stabilizing action can be evaluated, for example, by: the fact that precipitates of carrier particles derived from spontaneous aggregation are not observed after coexistence of receptor-sensitized insoluble carrier particles with the organic amine compound of the present invention takes place, followed by a predetermined period of a static state; or the fact that an optical change of the reagent containing the organic amine compound remains within a predetermined proportion before and after the static state. Based on the evaluation, the organic amine compound can be selected.

To be specific, when a latex is used as a receptor-sensitized carrier particle, the evaluation is performed in the following process. When coexistence of the receptor-sensitized carrier particles with the organic amine compounds takes place, followed by a predetermined period of a static state (for example, at 4° C. for 3 days or more), a ratio ($A_{600\ nm}/A_{800\ nm}$ ratio) of an absorbance at a wavelength of 600 nm to an absorbance at a wavelength of 800 nm before and after the static state is measured. Then, a value after the static state to a value before the static state (initial value) is relatively evaluated. Such organic amine compounds which are evaluated that a reduction rate of the value after the static state to the initial value does not show 30% or less have a stabilizing action, and those organic amine compounds can be preferably used. Moreover, organic amine compounds that show a reduction rate of 10% or less in the absorbance ratio are more preferable. Organic amine compounds that show a reduction rate of 5% or less in the absorbance ratio are most preferable.

The above process is carried out when a latex is used as a receptor-sensitized carrier particle. As described above, a stabilizing action of particle dispersibility can be easily evaluated. Therefore, the evaluation process described above may be used as a method of screening the organic amine compound of the present invention. To be specific, a method of selecting organic amine compounds having a stabilizing action can be exemplified, the stabilizing action being evaluated by the fact that a reduction rate of the value after the static state to the initial value does not show 30% or less in a ratio ($A_{600\ nm}/A_{800\ nm}$ ratio) of an absorbance at a wavelength of 600 nm to an absorbance at a wavelength of 800 nm, when the organic amine compounds are allowed to coexist with antibody-sensitized insoluble carriers at 4° C. for 3 days or more.

The term agglutination reaction in the present invention means an agglutination reaction derived from a specific binding between a receptor of a receptor-sensitized insoluble carrier particle and a target ligand. The term agglutination accelerating action means a function that coexistence of a receptor-sensitized insoluble carrier particle with a target ligand in a reagent easily causes specific agglutination. For example, the agglutination accelerating action can be confirmed as follows. The receptor-sensitized insoluble carrier particle is added to a sample containing a target ligand. Then, comparison is made between an absorbance measured in the state of addition of an organic amine compound and an absorbance measured in the state of no addition of an organic amine compound after a predetermined time. The agglutination accelerating action may be confirmed by whether the absorbance measured in the state of addition of an organic amine compound is higher than the absorbance measured in the state of no addition of an organic amine compound or not. As an agglutination accelerator, a substance having the same accelerating function as sodium chloride or better accelerating function is preferable. An organic amine compound having both the above-mentioned stabilizing action of particle dispersibility and the accelerating action of an agglutination reaction is more preferable. Screening a compound having those both functions can be desirably performed, in consideration of easiness of a measurement method, by: first investigating whether the compound has a stabilizing action of particle dispersibility; and then investigating whether the compound has an accelerating action of an agglutination reaction, because the above-mentioned steps can contribute to efficient screening of the compound.

In the foregoing, the case where a latex is used as a receptor-sensitized carrier particle was mainly described. Any suitable wavelength for measurement can be selected in consideration of a material or an average particle diameter of the carrier particle. In addition, an evaluation method using an absorbance ratio was described. The absorbance ratio can be replaced with any suitable means that those skilled in the art are able to use, such as the number of particles (precipitated particles yield contrasting density), measurement of particle sizes (aggregation results in a larger size), measurement of scattered light or measurement of absorption spectrum (aggregation results in an increase or a shift). Further, the optical detection can be replaced with an electrochemical detection to a possible extent.

(Buffer Solution)

The agglutination reaction in the present invention is performed in a buffer solution. A kind, a concentration, and a pH of the buffer solution in which the agglutination reaction is optimally performed are selected. A phosphate buffer solution, a Tris hydrochloride buffer solution, a carbonate buffer solution, a glycine buffer solution, a Good's buffer solution, or the like can be used. A concentration of a buffering agent in the buffer solution is adjusted in the range of about 5 mM to 500 mM. The buffer solution is frequently used in neutral to basic pH, and usually used in a pH between 7.0 and 9.5.

(Measurement Method for Agglutination Signal)

Measurement of an agglutination signal can be performed by any measurement method as long as the method is generally used for measurement of an agglutination reaction. Examples of the measurement method include absorbance measurement, particle number measurement, particle size measurement, and scattered light measurement.

Detection of the agglutination signal can be performed by a variety of the methods described above. A method using a commonly-used biochemical analyzer is convenient. For example, the method is specifically performed as below. To a sample containing a target ligand, a reagent containing an organic amine compound and a receptor-sensitized insoluble carrier particle such as a latex is added. The mixture is subjected to an incubation at a predetermined temperature for a predetermined time to measure absorbance during the incubation. A change amount of the absorbance is detected, whereby a concentration of the ligand in the test sample can be calculated based on a calibration curve prepared by using a standard solution whose concentration is known in advance as a sample. In a latex agglutination method, absorbance measured at wavelengths of 500 to 900 nm is usually used, and a change amount of absorbance during a reaction is commonly used for quantification.

(Constitution as Reagent for Measuring Agglutination)

The reagent for measuring agglutination can be prepared as a one-shot reagent obtained by allowing a reaction accelerator to preliminarily coexist with a receptor-sensitized latex, because the organic amine compound of the present invention is unlikely to cause spontaneous agglutination of the receptor-sensitized latex even in the coexistence of the both substances. Thus, the reagent for measuring agglutination can be constituted as the reagent for measuring agglutination formed of a one-shot reagent. When the reagent for measuring agglutination is prepared as a one-shot reagent, measurement is possible by a one-step reaction, so measurement time can be shortened up to half or less of measurement time required for a case using a conventional two-shot reagent. In addition, when a reaction is performed using the one-shot reagent in the same time as that required for measurement of the case using the conventional two-shot reagent, higher measurement sensitivity can be obtained. Therefore, by constituting the reagent as the reagent for measuring agglutination formed of a one-shot reagent, the effect of the present invention can be attained most effectively.

The organic amine compound of the present invention has a reaction accelerating effect, so a reagent for measuring agglutination can prepared as a conventional two-shot reagent to constitute of the reagent for measuring agglutination.

Use of salt, sugar, a protein, a surfactant, a preservative, and the like which are usually added to or used in a reagent for measuring agglutination is not restricted as long as the use thereof does not lower the effects of the present invention.

(Usage as Measuring Reagent)

The reagent for measuring agglutination of the present invention is excellent in a reaction accelerating effect of an agglutination reaction by an action of the used amine compound. Thus, the reagent enables reduction of a reaction time and consequently a measuring time, and/or improvement of measurement sensitivity. Therefore, the reagent can be used for increasing the number of measurement per a certain time as a reagent for measuring agglutination consisting of a one-shot reagent. The reagent can be also used for measurement of a ligand that was difficult for a conventional reagent consisting of two solutions to perform because of deficiency of measurement sensitivity.

Further, when two kinds of the one-shot reagents of the present invention are used in combination in a measurement system for a two-shot reagent, two kinds of ligands can be measured consecutively in the same reaction vessel. The following specific usage can be employed. That is, when the target ligand include two or more kinds, a time-dependent change of an agglutination reaction is measured, the reaction being caused by adding an insoluble carrier particle sensitized with a receptor R1 that specifically reacts with a ligand L1. Then, after the reaction becomes substantially steady, or after the reaction is allowed to be substantially steady or simultaneously when the reaction is allowed to be substantially steady, a time-dependent change of an agglutination reaction is measured, the reaction being caused by further adding an insoluble carrier particle sensitized with a receptor R2 that specifically reacts with a different ligand L2.

It can be easily presumed that the reaction of L1 and R1 should be substantially steady at the start of the reaction of L2 and R2 because the reaction of L1 and R1 affects measurement results of L2 and R2. When it is difficult for an amount (concentration) of the target ligand in the sample to preferably correspond to an amount (concentration) of the receptor-sensitized latex, the reaction of L1 and R1 can be adjusted to a steady state by, for example, adding a substance (may be free R1) that specifically reacts with L1 before the reaction of L2 and R2 starts.

The method of measuring two kinds of ligands consecutively in the same reaction vessel by using two kinds of the one-shot reagent of the present invention in combination is particularly effective for calculation of a PGI/PGII ratio required for determination of a content ratio of two kinds of ligands in the same sample and an examination of HbA1c or the like. Therefore, the method is completely novel.

Hereafter, the present invention will be described in more detail by Examples, but the present invention is not limited to the Examples.

EXAMPLES

Example 1

(Screening of Organic Amine Compound Having Stabilizing Action of Particle Dispersibility when Latex is Used as Insoluble Carrier Particle)

Figure 1:
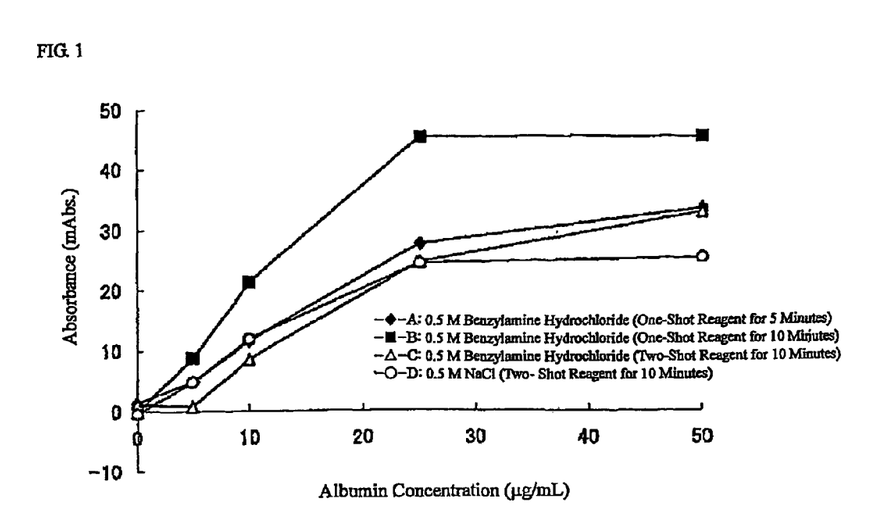
FIG. 1 is a graph showing the measurement results of albumin by means of a latex reagent for measuring albumin containing benzylamine hydrochloride.

Each of the various organic amine compounds shown in FIG. 1 was dissolved in each of 20 mM Tris buffer solutions (pH 7.0). The mixture was mixed with a latex reagent for measuring D-dimer (D-dimer latex reagent of nanopia D-dimer (2) (manufactured by Daiichi Pure Chemicals Co., Ltd.)) in a ratio of 1:1 to prepare a latex reagent containing an organic amine compound in a final concentration of 62.5 to 500 mM. Besides, another latex reagent prepared by using a 20 mM Tris buffer solution (pH 7.0) in the same way was used as a control. Further, for comparison, latex reagents each containing sodium chloride in final concentrations of 150, 300, and 500 mM were also prepared in the same way. Those reagents were left in a static state at 4° C. for 3 days. Then, each absorbance of the supernatant and the latex solution after being stirred was measured at wavelengths of 600 nm and 800 nm to calculate each of absorbance ratios ($A_{600\,nm}/A_{800\,nm}$ ratio). Table 1 shows the results of the concentration at which dispersion state was most preferable, and no latex precipitate occurred. Table 1 was made up based on the results that the absorbance ratio ($A_{600\,nm}/A_{800\,nm}$ ratio) and absorbance of the supernatant did not decrease, that is, particle precipitate caused by spontaneous agglutination was suppressed in the concentration range investigated about various kinds of organic amine hydrochlorides of 2-amino-2-thiazoline hydrochloride, benzylamine hydrochloride, benzamidine hydrochloride, guanidine hydrochloride, aminopyrine, antipyrine, 4-aminoantipyrine, o-phenylenediamine dihydrochloride, p-anisidine hydrochloride, diphenhydramine hydrochloride, 2,4-diaminoanisole dihydrochloride, pyridine hydrochloride, 1,4-phenylenediamine hydrochloride, aminoguanidine hydrochloride, and betaine hydrochloride.

Table 1 shows that there is difference of 30% or more between the result of the supernatant and that of after being stirred in the absorbance ratio ($A_{600\,nm}/A_{800\,nm}$ ratio, which is described as "600/800" in Table 1) of latex reagents each containing 150, 300, and 500 mM sodium chloride after a static state at 4° C. for 3 days. Further, Table 1 shows that the absorbance ratio of after being stirred is lowered by about 60% compared with that of the control. The results indicate that an antibody-sensitized latex cannot be stably stored in a dispersion state in the presence of sodium chloride that has been commonly used as an agglutination accelerator.

On the other hand, when the above-mentioned organic amine compounds were used, there was almost no difference between the absorbance ratio ($A_{600\,nm}/A_{800\,nm}$ ratio) of the supernatant and that of after being stirred, and the differences were 10% or less of the absorbance ratio of the control. The above results show that use of the organic amine compounds described above results in maintenance of the dispersion state of the antibody-sensitized latex and prevention of precipitate by spontaneous agglutination or the like.

Example 2

Measurement of Albumin Using Reagent for Measuring Albumin Containing benzylamine hydrochloride (1) Preparation of Anti-Albumin Antibody 100 μg of purified human albumin (manufactured by Sigma-Aldrich Corporation) was used for each of immunization. The initial immunization was performed by using 200 μL of emulsion prepared by mixing the albumin with complete Freund's adjuvant in the same amount, and the emulsion was injected into abdominal cavities of BALB/c mice. Additional immunization was performed by using 200 μL of emulsion prepared in the same manner except for mixing the albumin with incomplete Freund's adjuvant. The additional immunization was repeated three times with a two-week interval.

After ELISA was carried out to measure each of antibody titer in each blood obtained from mouse fundus veins, a mouse showing a high antibody value was selected and was

TABLE 1

| | Soon after suspension | | | After static state at 4° C. for 3 days | | | | | |
|---|---|---|---|---|---|---|---|---|---|
| | | | | Supernatant* | | | After being stirred* | | |
| Organic amine compound/absorbance | 800 nm | 600 nm | 600/800 | 800 nm | 600 nm | 600/800 | 800 nm | 600 nm | 600/800 |
| Control (no addition) | 0.486 | 1.466 | 3.02 | 92.2 | 91.6 | 99.3 | 98.6 | 98.9 | 100.2 |
| +500 mM 2-amino-2-thiazoline hydrochloride | 0.451 | 1.363 | 3.02 | 92.2 | 90.7 | 98.4 | 92.2 | 90.7 | 98.4 |
| +500 mM benzamidine hydrochloride | 0.442 | 1.339 | 3.03 | 92.3 | 90.0 | 97.5 | 92.0 | 90.3 | 98.1 |
| +500 mM benzylamine hydrochloride | 0.442 | 1.337 | 3.02 | 103.5 | 98.5 | 95.2 | 103.6 | 98.4 | 95.0 |
| +500 mM guanidine hydrochloride | 0.471 | 1.413 | 3.00 | 126.2 | 116.3 | 92.2 | 125.6 | 116.2 | 92.5 |
| +62.5 mM aminopyrine | 0.461 | 1.388 | 3.01 | 103.7 | 102.4 | 98.8 | 103.7 | 102.4 | 98.8 |
| +500 mM antipyrine | 0.434 | 1.311 | 3.02 | 97.6 | 98.3 | 100.8 | 98.1 | 98.1 | 100.0 |
| +500 mM 4-aminoantipyrine | 0.431 | 1.312 | 3.05 | 99.6 | 99.1 | 99.5 | 99.5 | 99.6 | 100.1 |
| +150 mM o-phenylenediamine dihydrochloride | 0.483 | 1.420 | 2.94 | 118.6 | 117.2 | 98.8 | 119.1 | 118.3 | 99.3 |
| +150 mM p-anisidine hydrochloride | 0.457 | 1.373 | 3.01 | 102.9 | 103.8 | 100.9 | 104.8 | 104.5 | 99.7 |
| +500 mM diphenhydramine hydrochloride | 0.339 | 1.021 | 3.01 | 103.4 | 102.5 | 99.1 | 104.0 | 103.0 | 99.0 |
| +150 mM 2,4-diaminoanisole dihydrochloride | 0.451 | 1.340 | 2.97 | 106.8 | 116.5 | 109.1 | 109.4 | 117.7 | 107.7 |
| +150 mM pyridine hydrochloride | 0.452 | 1.361 | 3.01 | 99.3 | 99.6 | 100.4 | 99.6 | 99.8 | 100.1 |
| +150 mM 1,4-phenylenediamine hydrochloride | 0.459 | 1.374 | 2.99 | 110.1 | 107.2 | 97.4 | 111.2 | 108.1 | 97.2 |
| +500 mM aminoguanidine hydrochloride | 0.465 | 1.398 | 3.01 | 123.2 | 111.2 | 90.2 | 123.7 | 111.2 | 89.9 |
| +150 mM betaine hydrochloride | 0.470 | 1.429 | 3.04 | 100.3 | 96.2 | 95.9 | 100.5 | 96.4 | 95.9 |
| +150 mM sodium chloride | 0.483 | 1.462 | 3.03 | 156.8 | 87.0 | 55.5 | 468.9 | 174.8 | 37.3 |
| +300 mM sodium chloride | 0.485 | 1.461 | 3.01 | 59.5 | 32.7 | 54.9 | 463.1 | 173.5 | 37.5 |
| +500 mM sodium chloride | 0.485 | 1.459 | 3.01 | 56.9 | 28.5 | 50.1 | 457.9 | 172.0 | 37.6 |

*rate (%) to absorbance and absorbance ratio soon after suspension used for cell fusion. After two weeks from the fourth immunization, 100 μg of albumin dissolved in 200 μL of physiologic saline was injected into mouse abdominal cavity, and spleen of the mouse was extirpated 3 days later. After the spleen was loosened in a RPMI1640 medium, the resultant was centrifuged at 1,500 rpm to collect spleen cells. After the cells were washed 3 times or more with a fetal bovine serum-free RPMI1640 medium, 2 mL of 15% fetal bovine serum-containing RPMI1640 medium were added, followed by suspension, to prepare a spleen cell suspension. After the spleen cells were mixed with myeloma cells, SP2/O-AG14, at a ratio of 6:1, the mixture was subjected to cell fusion in the presence of 50% polyethyleneglycol. The resultant was centrifuged at 1,500 rpm to collect a precipitate. The precipitate was suspended in a GKN solution (prepared by dissolving 2 g of glucose, 0.4 g of potassium chloride, 8 g of sodium chloride, 1.41 g of disodium hydrogenphosphate, and 0.78 g of sodium dihydrogenphosphate dihydrate in purified water to have 1 L of the GKN solution). The suspension was washed by centrifugation to collect a precipitate. The obtained precipitate was suspended in 30 mL of 15% fetal bovine serum-containing RPMI1640 medium. The suspension was aliquoted in 100 μL to each well of three 96-well microplates, and a HAT medium containing $2.5 \times 10^6$ cells/mL of BALB/c mouse thymocytes as feeder cells was also aliquoted in 200 μL to each well of three 96-well microplates. The resultant was cultured in a 5% carbon dioxide incubator at 37° C.

Existence of anti-albumin antibodies in the culture supernatant was confirmed by ELISA using albumin attached to a solid phase. Ten days later, proliferation of fused cells was confirmed in all the wells. To be specific, 100 μL of 10 mM phosphate buffer solution containing 10 μg/mL of albumin and 150 mM sodium chloride (pH 7.2, and being hereinafter abbreviated as PBS) were aliquoted to each well of a 96-well microplate, and the microplate was left standing at 4° C. overnight. Next, after the microplate was washed three times with 300 μL of PBS containing 0.05% Tween 20 and 1% bovine serum albumin, a culture supernatant of each well was added in 50 μL/well, and the mixture was left standing at room temperature for 1 hour. After that, the microplate was washed three times with PBS containing 0.05% Tween 20, and 50 μL/well of peroxidase-labeled anti-mouse antibody (manufactured by Daiichi Pure Chemicals Co., Ltd.) were added, and the mixture was left standing at room temperature for 1 hour. The microplate was washed three times with PBS containing 0.5% Tween 20, and 50 μL/well of citrate buffer solution (pH of 5) containing 0.2% o-phenylenediamine and 0.02% hydrogen peroxide were added. After the mixture was left standing at room temperature for 15 minutes, 50 μL/well of 4.5 N sulfuric acid were added to stop the reaction. Then absorbance was measured at a wavelength of 492 nm, and the wells showing high absorbance were selected.

Monocloning was carried out by a limiting dilution method. That is, to a 96-well microplate to which BALB/c mouse thymocytes cells were aliquoted in $10^6$ cells as feeder cells, a solution diluted so as to contain 10 cells/mL of hybridomas in a positive well were aliquoted in 0.1 mL. An HT medium was used for the first culture, and a 15% fetal bovine serum-containing RPMI1640 medium was used for the second culture and the following cultures. The culture was performed at 37° C. for 10 days in a 5% carbon dioxide incubator. 30 kinds of anti-albumin monoclonal antibody producing cells were obtained through a set of selected of positive cells by ELISA and monocloning operation by a limiting dilution method which was repeated three times. About $10^5$ cells each of the 30 kinds of cells were injected into each abdominal cavities of pristane-pretreated mice to collect generated ascites from each of the mice. Each of the collected ascites was subjected to centrifugation to remove insoluble substances. To each of the resultants, an equivalent amount of saturated ammonium sulfate solution was added. The mixture was left standing overnight while being stirred, and precipitates were collected by centrifugation. Each of the collected precipitates was dissolved in a 20 mM Tris buffer solution (pH 8.0) to dialyze with the buffer solution. Each of the dialyzed substances was independently adsorbed to DEAE-sepharose column equilibrated with the buffer solution. Subsequently, each of the IgG fractions obtained by eluting each of the adsorbed substances in accordance with concentration gradient of 0 to 300 mM sodium chloride in the buffer solution was dialyzed with 50 mM glycine buffer solution. Finally, 30 kinds of purified antibodies were obtained.

(2) Selection of Anti-Albumin Monoclonal Antibody

To each of 3 mL of 20 mM Tris buffer solutions (pH 8.5) containing each of 1.4 mg/mL of the purified antibodies, 3 mL of suspension containing 2% latex (manufactured by Sekisui Chemical Co., Ltd.) of 0.3 μm of average particle diameter were added, and each of the mixtures was stirred at 4° C. for 2 hours. To each of the resultants, 6 mL of 20 mM Tris buffer solution (pH 8.5) containing 0.4% bovine serum albumin were added, followed by stirring at 4° C. for 1 hour. After centrifugation, the supernatant was removed, and each of the precipitates was suspended again with 20 mM Tris buffer solution (pH 8.5) so as to attain an absorbance of 1 OD at a wavelength of 600 nm, whereby each of anti-albumin antibody sensitized latex solutions was prepared.

Next, to 100 μL of 20 mM Tris buffer solution (pH 8.5) containing 150 mM sodium chloride, 3 μL of the sample solution containing albumin were added, and the mixture was incubated at 37° C. for 5 minutes. To the mixture, 100 μL of two-kind combination (1:1 ratio mixed solution) of each of the above-mentioned anti-albumin antibody sensitized latex solutions were added, followed by stirring. Absorbance change amount for 5 minutes at the main wavelength of 570 nm and the sub-wavelength of 800 nm was measured, and the combination of antibodies showing the largest absorbance change was selected.

(3) Preparation of Latex Reagent for Measuring Albumin

The same operation as described above was performed by using 3 mL of 20 mM Tris buffer solution (pH 8.5) containing 1.4 mg/mL of the selected anti-albumin monoclonal antibodies to prepare a latex reagent for measuring albumin.

(4) Determination of Optimal Concentration of benzylamine hydrochloride

Latex reagents measuring albumin were prepared in such a manner that the reagents contain each of final concentrations of 150, 300, and 500 mM of benzylamine hydrochloride (manufactured by TOKYO KASEI KOGYO CO., LTD.), respectively. The prepared reagents were left in a static state at 4° C. for 3 days, and then, absorbances of the supernatant and the suspension of the reagents were measured at wavelengths of 600 nm and 800 nm to calculate the absorbance ratio ($A_{600\,nm}/A_{800\,nm}$ ratio, which is described as "600/800" in Table 2) (Table 2). According to the results, the best benzylamine hydrochloride concentration in the latex reagent for measuring albumin was determined as 500 mM. At the concentration of 500 mM, absorbance of the supernatant did not decrease when measurement of absorbance was performed, that is, particle precipitate caused by spontaneous agglutination was suppressed, and dispersion state of the particles was most preferable.

TABLE 2

| Reagent for measuring albumin | | 800 nm | 600 nm | 600/800 |
|---|---|---|---|---|
| control | | 0.7297 | 1.5746 | 2.16 |
| +150 mM benzylamine hydrochloride | supernatant | 0.2912 | 0.6358 | 2.18 |
| | after being stirred | 1.2363 | 1.9812 | 1.60 |
| +300 mM benzylamine hydrochloride | supernatant | 0.7180 | 1.5243 | 2.12 |
| | after being stirred | 0.8197 | 1.6854 | 2.06 |
| +500 mM benzylamine hydrochloride | supernatant | 0.7217 | 1.5523 | 2.15 |
| | after being stirred | 0.7277 | 1.5598 | 2.14 |

(5) Preparation of Latex Reagent for Measuring Albumin Containing benzylamine hydrochloride A latex reagent for measuring albumin containing benzylamine hydrochloride in a final concentration of 500 mM was prepared.

(6) Measurement of Albumin

To each of 200 μL of the latex reagents for measuring albumin containing benzylamine hydrochloride, each of 3 μL of the sample solutions containing 0 to 50 μg/mL of albumin was added, followed by stirring the mixture. Absorbance change amounts were measured at the main wavelength of 570 nm and sub-wavelength of 800 nm at 37° C. for 5 minutes (A in FIG. 1) and for 10 minutes (B in FIG. 1).

(7) Comparative Example

To each of 100 μL of 20 mM Tris buffer solutions (pH 8.5) containing 500 mM benzylamine hydrochloride or 500 mM sodium chloride, each of 3 μL of the sample solutions containing 0 to 50 μg/mL of albumin was added, followed by incubating the mixture at 37° C. for 5 minutes. Then, each of 100 μL of the above-mentioned latex reagents for measuring albumin was added and stirred. Absorbance change amounts were measured at the main wavelength of 570 nm and sub-wavelength of 800 nm at 37° C. for 5 minutes (C and D in FIG. 1).

(8) Results

FIG. 1 shows that measurement sensitivity at the time of measurement for 5 minutes using a one-shot reagent with benzylamine hydrochloride (A in FIG. 1) is similar to measurement sensitivity at the time of measurement for 10 minutes using a two-shot reagent (C in FIG. 1), which is a conventional measurement method, even though the reaction time of the one-shot reagent is half the time of the two-shot reagent, and measurement sensitivity at the time of measurement for 5 minutes using a one-shot reagent is also similar to measurement sensitivity at the time of measurement using sodium chloride (D in FIG. 1). Therefore, the one-shot reagent with benzylamine hydrochloride enables significant reduction of measurement time. In addition, measurement sensitivity at the time of using one-shot reagent for 10 minutes (B in FIG. 1) shows a large increase compared with measurement sensitivity at the time of using two-shot reagent for 10 minutes (C in FIG. 1). The result shows that large increase in measurement sensitivity can be attained when measurement is performed in the same amount of time as conventional measurement.

Example 3

Figure 2:
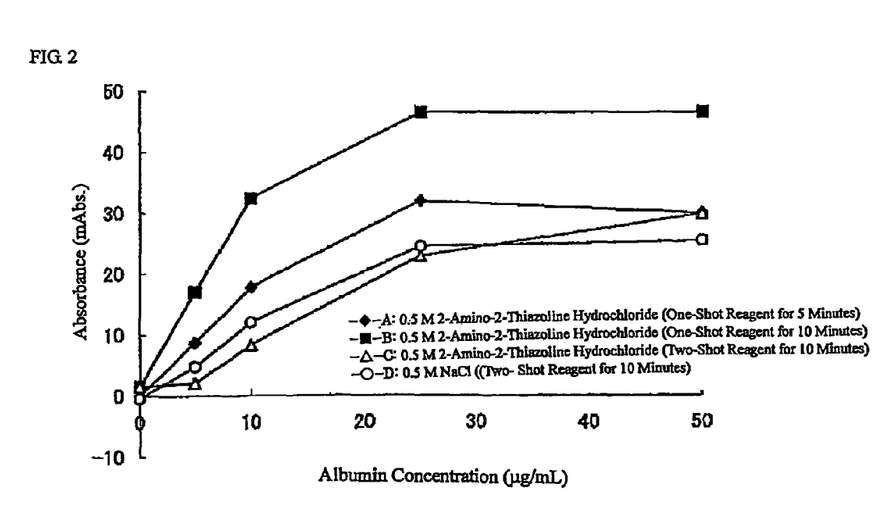
FIG. 2 is a graph showing the measurement results of albumin by means of a reagent for measuring albumin containing 2-amino-2-thiazoline hydrochloride.

Measurement of Albumin with Reagent for Measuring Albumin Containing 2-amino-2-thiazoline hydrochloride A reagent was prepared in the same manner as the above-mentioned Example 1 except that 2-amino-2-thiazoline hydrochloride was used as an organic amine compound to measure albumin. The results are shown in FIG. 2. FIG. 2 indicates that 2-amino-2-thiazoline hydrochloride has the similar effect to benzylamine hydrochloride.

Example 4

Measurement of Albumin with Reagent for Measuring Albumin Containing Benzamidine Hydrochloride A reagent was prepared in the same manner as the above-mentioned Example 1 except that benzamidine hydrochloride was used as an organic amine compound to measure albumin. The results are shown in FIG. 3.

Figure 3:
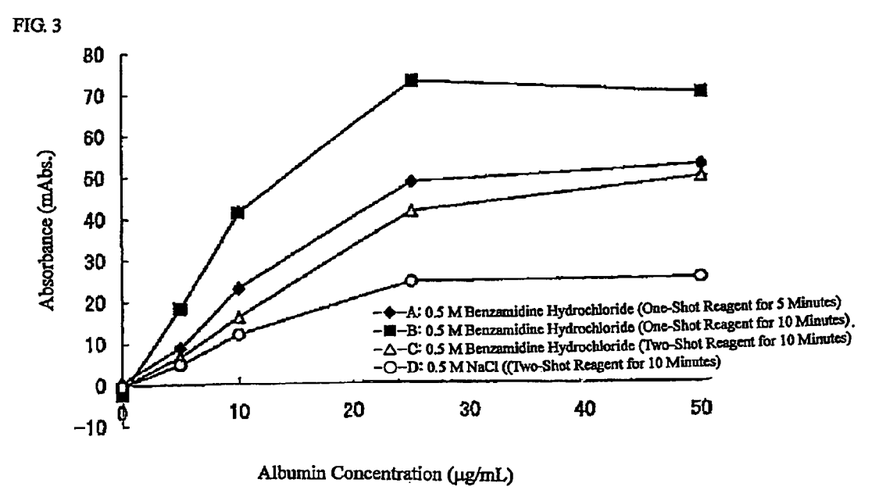
FIG. 3 is a graph showing the measurement results of albumin by means of a reagent for measuring albumin containing benzamidine hydrochloride.

FIG. 3 indicates that the one-shot reagent obtained by using benzamidine hydrochloride in the same method as that using benzylamine hydrochloride enables significant reduction of measurement time, and large increase in measurement sensitivity can be attained when measurement is performed in the same amount of time as conventional measurement. FIG. 3 also indicates that large increase in measurement sensitivity has been attained only by using benzamidine hydrochloride instead of sodium chloride (C in FIG. 3) compared with the case where sodium chloride that is a conventional reaction accelerator is used (D in FIG. 3).

INDUSTRIAL APPLICABILITY

The present invention can provide a reagent for measuring agglutination of ligands, the reagent being excellent in stability and measurement sensitivity as a reagent. Further, the present invention can provide the reagent as a one-shot reagent when receptor-sensitized carrier particles are allowed to preliminarily coexist with a reaction accelerator.

Particularly, when the reagent is prepared as a one-shot reagent, measurement can be performed simply, and reduction of reaction time can be attained. That is, measurement sensitivity of the measurement performed using the one-shot reagent in the same amount of time as the conventional measurement is increased. Besides, use of two kinds of the one-shot reagents in combination can provide a reagent that is capable of measuring two kinds of ligands consecutively in the same reaction vessel. Therefore, the reagent is very useful as a breakthrough measurement reagent in the clinical examination field.

The invention claimed is:
1. A reagent solution for measuring agglutination, comprising:
    an insoluble carrier particle sensitized only with a receptor specifically reacting with a target ligand, and
    one or more organic amine compounds selected from the group consisting of 2-amino-2-thiazoline hydrochloride, benzamidine hydrochloride, benzylamine hydrochloride, aminopyrine, antipyrine, 4-aminoantipyrine, o-phenylenediamine dihydrochloride, p-anisidine hydrochloride, diphenhydramine hydrochloride, 2,4-diaminoanisole dihydrochloride, pyridine hydrochloride, and 1,4-phenylenediamine hydrochloride, wherein the insoluble carrier particle is a latex particle, and wherein the receptor is an antibody selected from the group consisting of a polyclonal antibody, a monoclonal antibody, and a fragment thereof comprising a reactive site for the target ligand, wherein the organic amine compound has a concentration of 50 mM to 1,000 mM in the reagent solution.

2. The reagent solution for measuring agglutination according to claim 1, wherein the target ligand is any one or more of the ligands selected from the group consisting of C-reactive protein (CRP), fibrin/fibrinogen degradation products (FDP), D-dimer, prostate-specific antigen (PSA), hemoglobin A1c, albumin, pepsinogen I (PGI), pepsinogen II (PGII), matrix metalloproteinase (MMP), trypsin, chymotrypsin, elastase, and cathepsin.

3. The reagent solution for measuring agglutination according to claim 1, wherein the organic amine compound has an accelerating action of an agglutination reaction and a stabilizing action of particle dispersibility.

4. The reagent solution for measuring agglutination according to claim 1, wherein the organic amine compound is 2-amino-2-thiazoline hydrochloride.

5. The reagent solution for measuring agglutination according to claim 1, wherein the organic amine compound is benzamidine hydrochloride.

6. The reagent solution for measuring agglutination according to claim 1, wherein the organic amine compound is benzylamine hydrochloride.

7. The reagent solution for measuring agglutination according to claim 1, wherein the organic amine compound is aminopyrine.

8. The reagent solution for measuring agglutination according to claim 1, wherein the organic amine compound is antipyrine.

9. The reagent solution for measuring agglutination according to claim 1, wherein the organic amine compound is 4-aminoantipyrine.

10. The reagent solution for measuring agglutination according to claim 1, wherein the organic amine compound is o-phenylenediamine dihydrochloride.

11. The reagent solution for measuring agglutination according to claim 1, wherein the organic amine compound is p-anisidine hydrochloride.

12. The reagent solution for measuring agglutination according to claim 1, wherein the organic amine compound is diphenhydramine hydrochloride.

13. The reagent solution for measuring agglutination according to claim 1, wherein the organic amine compound is 2,4-diaminoanisole dihydrochloride.

14. The reagent solution for measuring agglutination according to claim 1, wherein the organic amine compound is pyridine hydrochloride.

15. The reagent solution for measuring agglutination according to claim 1, wherein the organic amine compound is 1,4-phenylenediamine hydrochloride.

16. The reagent solution for measuring agglutination according to claim 1, wherein the insoluble carrier particle sensitized with the receptor specifically reacting with the target ligand and the organic amine compound are in a state of coexistence.

17. The reagent solution for measuring agglutination according to claim 1, wherein the reagent comprises two insoluble carrier particles, wherein each insoluble carrier particle is sensitized with the receptor that specifically reacts with the target ligand, and wherein the target ligand comprises two or more kinds of ligands.

18. A reagent solution for measuring agglutination, consisting of:
an insoluble carrier particle sensitized only with a receptor specifically reacting with a target ligand, and
one or more organic amine compounds selected from the group consisting of 2-amino-2-thiazoline hydrochloride, benzamidine hydrochloride, benzylamine hydrochloride, aminopyrine, antipyrine, 4-aminoantipyrine, o-phenylenediamine dihydrochloride, p-anisidine hydrochloride, diphenhydramine hydrochloride, 2,4-diaminoanisole dihydrochloride, pyridine hydrochloride, and 1,4-phenylenediamine hydrochloride,
wherein the insoluble carrier particle is a latex particle, and wherein the receptor is an antibody selected from the group consisting of a polyclonal antibody, a monoclonal antibody, and a fragment thereof comprising a reactive site for the target ligand, wherein the organic amine compound has a concentration of 50 mM to 1,000 mM in the reagent solution;
a suitable buffer therefor;
water; and
optionally one or more of a salt, a sugar, a surfactant or a preservative.

19. A method of measuring a time-dependent change of an agglutination reaction caused by adding to a target ligand a solution containing an insoluble carrier particle sensitized only with a receptor that specifically reacts with the ligand, comprising:
allowing an organic amine compound to coexist at least when the reaction is performed,
wherein the organic amine compound is selected from the group consisting of 2-amino-2-thiazoline hydrochloride, benzamidine hydrochloride, benzylamine hydrochloride, aminopyrine, antipyrine, 4-aminoantipyrine, o-phenylenediamine dihydrochloride, p-anisidine hydrochloride, diphenhydramine hydrochloride, 2,4-diaminoanisole dihydrochloride, pyridine hydrochloride, and 1,4-phenylenediamine hydrochloride,
wherein the insoluble carrier particle is a latex particle, and wherein the receptor is an antibody selected from the group consisting of a polyclonal antibody, a monoclonal antibody, and a fragment thereof comprising a reactive site for the target ligand, wherein agglutination from an immunoreaction is measured, wherein the organic amine compound has a concentration of 50 mM to 1,000 mM in the solution.

20. The measurement method according to claim 19, wherein the insoluble carrier particle and the organic amine compound are preliminarily allowed to coexist.

21. The measurement method according to claim 20, wherein the target ligand includes two or more kinds, a time-dependent change of an agglutination reaction is measured, the reaction being caused by adding an insoluble carrier particle sensitized with a receptor R1 that specifically reacts with a ligand L1, and a time-dependent change of an agglutination reaction is measured, the reaction being caused by further adding an insoluble carrier particle sensitized with a receptor R2 that specifically reacts with a different ligand L2 after the reaction becomes substantially steady, or after the reaction is allowed to be substantially steady or simultaneously when the reaction is allowed to be substantially steady.

22. The measurement method according to claim 21, wherein a method of allowing the reaction to be substantially steady is performed by adding the R1 specifically reacting with the L1 in a free state.

23. A method of stabilizing particle dispersibility of a reagent solution for measuring agglutination, comprising:
- adding an organic amine compound to the reagent solution for measuring agglutination, wherein the organic amine compound is selected from the group consisting of 2-amino-2-thiazoline hydrochloride, benzamidine hydrochloride, benzylamine hydrochloride, aminopyrine, antipyrine, 4-aminoantipyrine, o-phenylenediamine dihydrochloride, p-anisidine hydrochloride, diphenhydramine hydrochloride, 2,4-diaminoanisole dihydrochloride, pyridine hydrochloride and 1,4-phenylenediamine hydrochloride,
- wherein the reagent solution comprises an insoluble carrier particle sensitized with a receptor specifically reacting with a target ligand,
- wherein the insoluble carrier particle is a latex particle, and
- wherein the receptor is an antibody selected from the group consisting of a polyclonal antibody, a monoclonal antibody, and a fragment thereof comprising a reactive site for the target ligand, wherein the organic amine compound has a concentration of 50 mM to 1,000 mM in the reagent solution.

* * * * *